(12) United States Patent
Fell et al.

(10) Patent No.: US 7,867,235 B2
(45) Date of Patent: Jan. 11, 2011

(54) SYSTEM AND METHOD FOR JOINT RESTORATION BY EXTRACAPSULAR MEANS

(76) Inventors: Barry M. Fell, 7124 Red Top Rd., Hummelstown, PA (US) 17036; Trevor Thomas Fell, 7124 Red Top Rd., Hummelstown, PA (US) 17036

( * ) Notice: Subject to any disclaimer, the term of this patent is extended or adjusted under 35 U.S.C. 154(b) by 201 days.

(21) Appl. No.: 11/917,244

(22) PCT Filed: Jun. 14, 2006

(86) PCT No.: PCT/US2006/023272
§ 371 (c)(1),
(2), (4) Date: Dec. 12, 2007

(87) PCT Pub. No.: WO2006/138439
PCT Pub. Date: Dec. 28, 2006

(65) Prior Publication Data
US 2008/0294269 A1    Nov. 27, 2008

Related U.S. Application Data

(60) Provisional application No. 60/690,375, filed on Jun. 14, 2005.

(51) Int. Cl.
*A61F 5/00* (2006.01)

(52) U.S. Cl. .................. 606/86 R; 606/60; 600/587

(58) Field of Classification Search .................. 128/898; 600/587; 606/57, 59, 65, 86 R, 87–105; 623/23.11–23.12, 23.15, 23.48
See application file for complete search history.

(56) References Cited

U.S. PATENT DOCUMENTS

| | | | | |
|---|---|---|---|---|
| 4,432,358 | A * | 2/1984 | Fixel | 606/66 |
| 4,456,005 | A * | 6/1984 | Lichty | 606/60 |
| 4,978,348 | A * | 12/1990 | Ilizarov | 606/57 |
| 5,007,910 | A * | 4/1991 | Anapliotis et al. | 606/65 |
| 5,270,300 | A * | 12/1993 | Hunziker | 514/12 |
| 6,033,412 | A * | 3/2000 | Losken et al. | 606/105 |
| 6,200,324 | B1 * | 3/2001 | Regni, Jr. | 606/105 |
| 6,607,561 | B2 * | 8/2003 | Brannon | 623/23.11 |
| 6,648,639 | B2 * | 11/2003 | Mao | 433/18 |
| 6,730,087 | B1 * | 5/2004 | Butsch | 606/57 |
| 6,827,720 | B2 * | 12/2004 | Leali | 606/96 |
| 6,849,076 | B2 * | 2/2005 | Blunn et al. | 606/105 |
| 2006/0190078 | A1 * | 8/2006 | Fell | 623/14.12 |

* cited by examiner

*Primary Examiner*—Thomas C Barrett
*Assistant Examiner*—Larry E. Waggle, Jr.
(74) *Attorney, Agent, or Firm*—Brooks Kushman P.C.

(57) ABSTRACT

A system and method for joint restoration by extracapsular means includes an actuator operable to apply a force to a portion of a bone to effect a change in the joint space geometry. One embodiment of the system includes an actuator operable to apply a cyclic loading to subchondral bone of a femur, wherein loads of a predetermined magnitude are alternately applied and released. Between periods of cyclic loading, rest periods are provided where no load is applied. Over time, the femoral joint surface is remodeled in accordance with the location, direction, magnitude, and frequency of the loading.

17 Claims, 5 Drawing Sheets

SYSTEM AND METHOD FOR JOINT RESTORATION BY EXTRACAPSULAR MEANS

CROSS-REFERENCE TO RELATED APPLICATIONS

This application claims the benefit of U.S. provisional application Ser. No. 60/690,375 filed Jun. 14, 2005, which is hereby incorporated herein by reference.

BACKGROUND OF THE INVENTION

1. Field of the Invention

The present invention relates to a system and method for joint restoration by extracapsular means, and more particularly to a system and method for corrective displacement of bone by extracapsular means.

2. Background Art

Figure 1A:
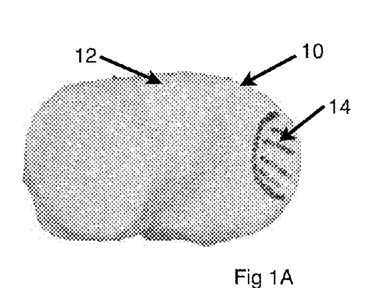
FIG. 1A shows a proximal end of a tibial plateau having an area of lost articular material.
Figure 1B:
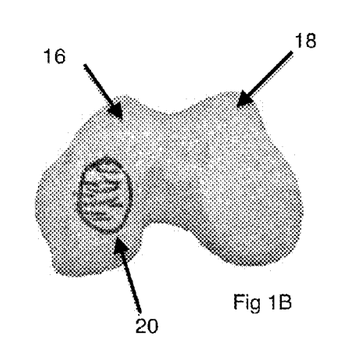
FIG. 1B shows a distal end of a mating femur for the tibia shown in FIG. 1, the femur having a condyle exhibiting lost articular material.

In the typical patient with osteoarthritis (OA) of the weight bearing joints, the disease is often described in terms of the missing articular material that covers the joint surface. In more advanced stages of the disease, the subchondral bone which underlies the articular material is often described as being "eroded" or deformed. In the typical patient with moderate to severe stages of the disease, the combination of missing articular material and deformed subchondral bone can lead to the joint having excessive joint laxity where there is excessive joint spacing, often 2-6 millimeters (mm), and occasionally as much as 10 mm. The areas of lost articular material and deformed subchondral bone in a typical patient with medial compartment OA of the knee are shown in FIGS. 1A and 1B. As the articular covering wears away, the loading in the joint changes towards excessive in the joint compartment that is losing the articular surface. As the load is increasing, the subchondral bone reacts to the increasing loads by changing its shape, thus adapting to handle the increasing loads. It will often thicken in the area directly under the areas of highest loads, and will generate osteophyte formation to increase the area of bone carrying the increased loads.

It has been demonstrated in literature that bone is constantly resorbing and rebuilding in response to biophysical stimuli—see, e.g., Chuanyong Qu, et al., *A Hypothetical Mechanism of Bone Remodeling and Modeling Under Electromagnetic Loads*, Biomaterials 27, 4050-4057 (2006). Osteocytes sense the increased strain environment, and respond accordingly. When bone tissue is damaged as in the micro-cracking that occurs in the presence of excessive stress or strain, osteoclasts remove the necrotic osteocytes. This activates growth factors held in the osteocytes, such as bone morphogenic protein (BMP) or transforming growth factor (TGF) beta 1. These growth factors are then released into the bone fluid, subsequently stimulating osteoblasts, which in turn, start the process of manufacturing new bone. Id. A strain response threshold limit is that point where the bone will react to the loads and begin to remodel. This is somewhat analogous to an industrial manufacturing technique known as "Incremental Sheet Forming" (ISF). This technique is used to form complex shapes from flat metal without the use of tooling. A "Forming Limit Diagram" (FLD) is created that represents the local limit strains. Strains above the limit represent failure, and below the limit they represent deformation of the material. Deformation limits utilizing this technique are much higher than using the macroscopic method represented by matched tool presses—see, e.g., L. Lamminen, et al., *Incremental Sheet Forming with an Industrial Robot*, Materials Forum 29, 331-335 (2005).

Similarly, when bone is measured on a large scale, it exhibits very classical (single elastic constant) behavior, but when the scale is reduced down to the trabecular level or below, the behavior becomes much more viscoelastic in nature, and tends to follow a Cosserat (multiple elastic constants) curve. This allows for much higher than predicted (by the classical approach) strain limits before failure occurs—see, e.g., Rod Lakes, *On the Torsional Properties of Single Osteons*, adapted from J. Biomechanics 28, 1409-1410 (1995). In order for bone formation to be initiated, the magnitude of mechanical strain of the bone must surpass some threshold. Therefore, for restorative remodeling to occur, this threshold must be exceeded, while not causing failure—see, e.g., Yeou-Fang Hsieh, et al., *Mechanical Loading of Diaphyseal Bone In Vivo: The Strain Threshold for an Osteogenic Response Varies with Location*, J. of Bone and Mineral Research 16, 2291-97 (2001).

In general, bones are made up of a number of different types of osseous material—e.g., trabecular (cancellous), subchondral, and cortical bone. An example of cortical bone is found in the shaft of a femur. Trabecular bone can be found inside the condylar region of a femur, and alongside the cortical bone. The trabecular bone transfers the loads from the subchondral bone to the cortical bone, and the subchondral bone is that bone which supports the articular regions of the joint surfaces. Each different type of bone may undergo different deformation mechanisms. For example, cortical bone in particular exhibits "cement line slippage" between the osteons, which accounts for an ISF type (almost viscoelastic) behavior when applied to localized regions. This is typically considered the reason bone is a "tough, non-brittle" material. It is also a response that is dependent on the direction of the applied load—a result of the oriented structure of bone—see, e.g., Rod Lakes, *On the Torsional Properties of Single Osteons*, adapted from J. Biomechanics 28, 1409-1410 (1995).

One of the mechanisms of bone deformation is "creep". Creep is a viscoelastic response defined as a time dependent strain under constant load. At sufficiently high stress levels, deformation will occur with time, leading to "creep-failure", or deformation that does not recover once the load is removed. The creep response of bone is significantly larger in younger bones as compared to older bones. In the mature skeleton, osteogenesis is initiated only if a mechanical load is applied; however, the bone quickly gets desensitized to mechanical loading and stops responding. Therefore, static loading may not be as effective in remodeling the bones older patients, as compared to younger patients—see, e.g., P. Zioupos and J. D. Currey, *Changes in the Stiffness, Strength, and Toughness of Human Cortical Bone with Age*, Bone 22(1), 57-66 (1998).

In addition to the magnitude of the stress, the rate of loading can also significantly affect the strain experienced by the bone. For example, a more rapid load onset results in a more rapid bone change. Conversely, a slower application of a load results in a smaller change, but thickening of the bone to handle the higher stress. Thus, a static load may build more dense bone, but a dynamic load may cause greater overall deformation of the bone. Another parameter that can affect the strain response of the bone is the number of cycles during which a load is applied—although this does not seem to have as pronounced an effect as changing the magnitude of the load—see, e.g., C. Rubin, et al., *Mechanical Strain, Induced Noninvasively in the High-Frequency Domain, Is Anabolic to Cancellous Bone, But Not Cortical Bone*, Bone 30, 445-452 (2002) and D. B. Burr, et al., *Bone Remodeling in Response to In Vivo Fatigue Microdamage*, J. Biomechanics 18(3), 189-

200 (1985). In addition, variation in rest periods—i.e., the length of time between either cyclically or statically applied loads—can also affect bone response. For example, rest periods may be required in order for the bone to respond to loads. Such rest periods can significantly increase the bone's anabolic response to mechanical loading—see, e.g., Charles H. Turner and Alexander G. Robling, *Exercise as an Anabolic Stimulus for Bone*, Current Pharmaceutical Design 10(21), 2629-41 (2004) and Sekou Singare, et al., *The Effect of Latency on Bone Lengthening Force and Bone Mineralization: An Investigation Using Strain Gauge Mounted on Internal Distractor Device*, Biomedical Engineering Online 5:18 (2006).

Conventional treatments of bone loss resulting from OA all have inherent limitations. For example, one such treatment used as a response to this loss of bone and the overlying cartilage is to remove even more subchondral bone, and replace it with a metal and plastic implant—the metal acting as a substitute for the bone, and the plastic acting as a substitute for the cartilaginous bearing surface. The unicompartmental knee replacement (UKR) and total knee replacement (TKR) are typical examples of such bone cutting treatment modalities. A high tibial osteotomy or femoral osteotomy may correct the angular misalignment by altering the load path with resection of bone elements extraneous to the joint capsule, but it does not address the issue of the excessive joint space. An interpositional spacer (for example, as described in U.S. Pat. Nos. 6,206,927 and 6,558,421) addresses the excessive joint space with the thickness of the device without requiring bone resection, but may still require the removal of some remaining articular material in order to achieve an adequate bearing surface for the device.

Therefore, a need exists for a system and method of corrective bone displacement that overcomes the limitations of prior art systems and methods by taking advantage of the bone's ability to remodel in the presence of an applied load.

SUMMARY OF THE INVENTION

The present invention includes a system and method for the corrective shaping of diseased, eroded subchondral bone normally found in the joint of a patient with osteoarthritis via extracapsular means—i.e., from outside the joint capsule, and generally without penetrating the joint capsule. The system and method described herein allow for the restoration of joint space geometry by applying a force to the underlying side of the bearing surface of the joint via mechanical or equivalent means utilizing a minimally invasive surgical procedure.

The method includes forcing the subchondral bone back to a configuration that is similar to its original shape and functionality prior to the effects of the OA, thus eliminating some or all of the excessive joint space.

The system and method according to the present invention can also be used in conjunction with other cartilage resurfacing techniques such as osteochondral transplants, chondrocyte "seeding" and other such methods. The present invention augments these techniques, which, by themselves, may not be able to provide additional bone—e.g., grafted bone—in sufficient thickness to correct joint misalignment. Thus, a combination of the system and method of the present invention and articular resurfacing techniques may be used to restore a joint with OA back to its original or near original functionality. In general, any bone, even those external to the joint area, such as the shaft of the tibia or femur, can be remodeled or even lengthened using embodiments of this invention.

According to one aspect of the present invention, the system components described herein can take advantage of the properties of bone that allow the bone to deform under constant stress via a "creep" or plastic deformation mechanism. The system components can push on the underside—e.g., the trabecular side—of the deformed subchondral bone, forcing a change of surface dimension on the joint surface (opposing) side of the subchondral bone. The subchondral bone may be softened to facilitate the reshaping process by drilling, cracking, laser etching, ultrasonically, biologically or by chemically treating the subchondral or the underlying cancellous bone, or by any other means in conjunction with the use of the system of the present invention, either to facilitate the initial movement, or during subsequent treatments. The devices according to the present invention may be permanently implanted in the bone, or can be removed after the desired results are obtained.

The present invention contemplates the application of force to the subchondral bone by any method effective to produce the desired result. For example, a relatively static load may be applied, wherein an initial force is imparted to the bone, and then after a period of time during which the articular surface changes dimension, the force can be increased to effect additional surface remodeling. Alternatively, a cyclic load can be imparted on the subchondral bone, with various parameters such as cycle frequency, rest periods, and force, being adjusted as desired to effect different remodeling modalities. It is worth noting that unless otherwise defined, the term "static load" as used herein does not imply that a load that can or will never change; rather, the term refers to a load that is either constant for some period of time, or a load that is applied so slowly as to approximate a constant load. This is distinguished from a dynamic load, which may be a single load applied very quickly, or may be a cyclic load of constant amplitudes and/or frequency, or one of varying amplitudes and/or frequency. To the extent that a dynamic load is quickly applied, and then maintained, the remaining load may effectively be a static load.

DETAILED DESCRIPTION OF THE PREFERRED EMBODIMENT(S)

As required, detailed embodiments of the present invention are disclosed herein; however, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a representative basis for teaching one skilled in the art to variously employ the present invention.

As described above, FIG. 1A shows a proximal end 10 of a tibia 12 having an area 14 of lost articular material. Similarly, FIG. 1B shows the distal end 16 of a femur 18 having an area 20 of lost articular material, corresponding to the area 14 on the tibia 12. To address this problem, one embodiment of the present invention provides a system 22, shown in FIG. 2. The system 22 includes a housing 24 that can be screwed or otherwise attached to the bony structure opposing the diseased area. The housing 24 may be constructed from metal, plastic, or any other suitable material. According to one aspect of the present invention, the housing may be capable of bony (biologic) ingrowth for additional stability. In the embodiment shown in FIG. 2, the housing 24 has external threads 26 to facilitate fixation to the bone; however, a housing, such as the housing 24, can also be fitted with interior or exterior flanges, or other mechanisms, to increase its fixation to the surrounding bone. In addition, more than one of these structures can be used together to provide even greater fixation.

Figure 3:
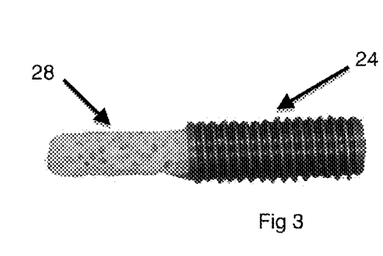
FIG. 3 shows one embodiment of a portion of the system shown in FIG. 2, including a housing and an extendable component.
Figure 4:
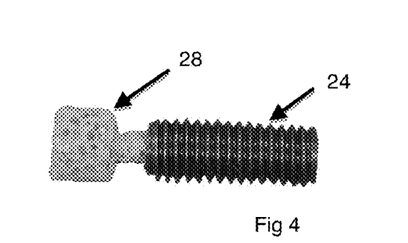
FIG. 4 shows the extendable component in a deformed state after insertion into a joint.

The system 22 also includes an extendable component 28, configured as an elongate member. The extendable component 28 is configured to be disposed inside the housing 24, in such a way that it extends from the housing 24 toward the underside of the diseased area of a bone—see, e.g., FIG. 3. The extendable component 28 may be capable of maintaining its shape, or deforming, such as to another predetermined shape. This is shown in FIG. 4, where the extendable component 28 has decreased in length and increased in width after contact with a solid surface, such as subchondral bone. According to one aspect of the present invention, this deformation may better distribute the bone altering forces over a desired area and may avoid a high concentration of force.

In one embodiment, the extendable component 28 may be made from trabecular metal or another material that is capable of biologic ingrowth. Of course, the extendable component 28 could alternatively be constructed of metal, plastic, or another suitable material. According to one aspect of the present invention, the extendable component 28 may be configured to be incapable of rotation while it is being extended and pressure is being applied. This will help to prevent the breaking of its biological ingrowth with cancellous bone. This can be achieved, for example, by configuring the inside of the housing 24 and the outside of the extendable component 28 with an non-circular cross section—e.g., a hexagonal cross section.

Figure 2:
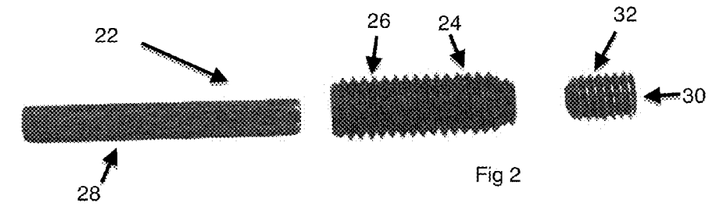
FIG. 2 shows a system in accordance with the present invention, which can be used with the damaged knee shown in FIG. 1.

To effect movement of the extendable component 28, the system 22 also includes a pressure screw 30—see FIG. 2. The pressure screw 30 includes external threads 32 configured to mate with internal threads (not visible in FIG. 2) inside the housing 24. As described more fully below in accordance with a method of the present invention, the insertion of the pressure screw 30 into the housing 24 forces the extendable portion toward the underside of a joint, thereby applying a force to the joint surface from the trabecular side. Components of a system according to the present invention, for example, the system 22, can have any dimensions suitable for their intended purpose. Moreover, while the system and method according to the present invention are shown and described herein as being implemented with respect to a knee joint, it is understood that the system and method could be utilized in body joints other than the knee such as, but not limited to, the hip, shoulder, wrist, ankle, or elbow.

Figure 5:
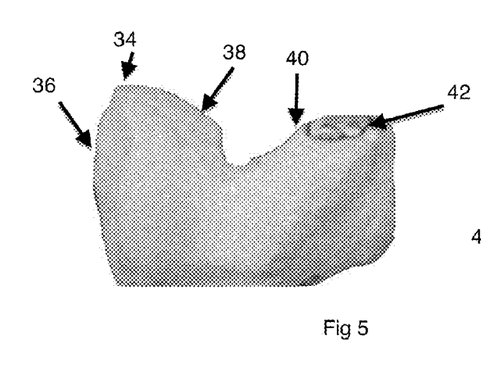
FIG. 5 shows a distal end of a femur identified for application of a method in accordance with the present invention.
Figure 6:
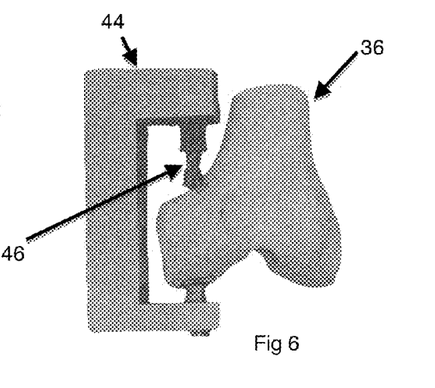
FIG. 6 shows the application of a drill guide and drill to the femur shown in FIG. 5.

FIGS. 5-12 detail a procedure for use and implantation of the system 22 according to the present invention. FIG. 5 shows the distal end 34 of a femur 36 having condyles 38, 40. On the condyle 40, an area 42 is identified, for example, during arthroscopic surgery, or with the aid of x-ray or other noninvasive imaging techniques. A drill guide 44, shown in FIG. 6, may be employed to mark the location of an entry hole for the housing 24. Alternatively, Computer Aided Surgery (CAS) techniques may be employed to place reference markers on the anatomy, and thus guide the insertion of the system 22 by electromagnetic, infrared (IR) or other means. In the embodiment shown in FIG. 6, a drill 46 of the appropriate size is used to drill out the underlying bony material to a predetermined depth. According to one aspect of the present invention, the subchondral bone should not be penetrated, although in certain extreme cases of deformity or fracture, this may be necessary for support or stability.

Figure 7:
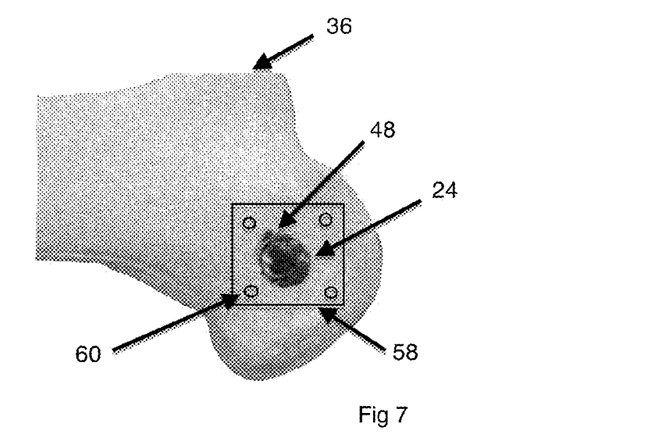
FIG. 7 shows a housing from the system shown in FIG. 2, the housing being inserted into a drilled hole in the femur of FIGS. 5 and 6.
Figure 8:
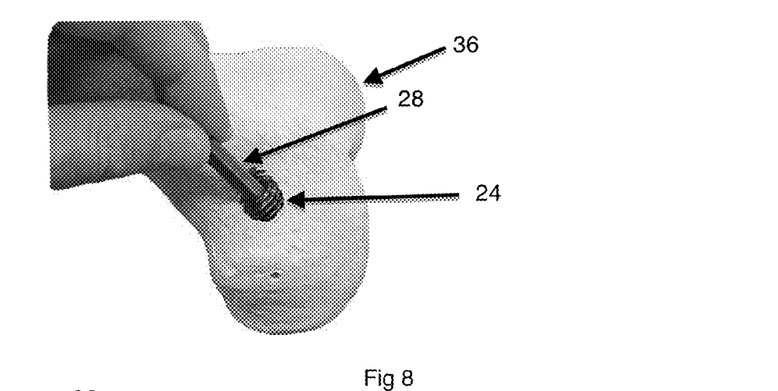
FIG. 8 shows the insertion of an extendable component into the housing shown in FIG. 7.
Figure 9:
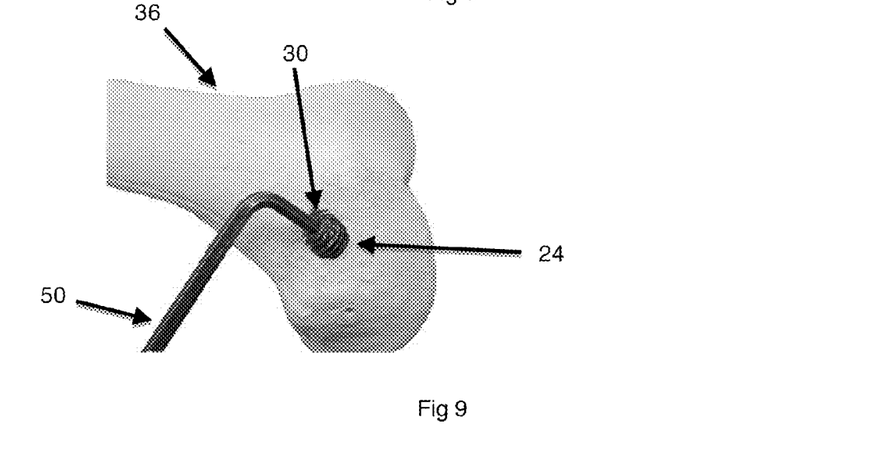
FIG. 9 shows the insertion of a pressure screw into the housing shown in FIGS. 7 and 8 to apply a force to the extendable component.
Figure 10:
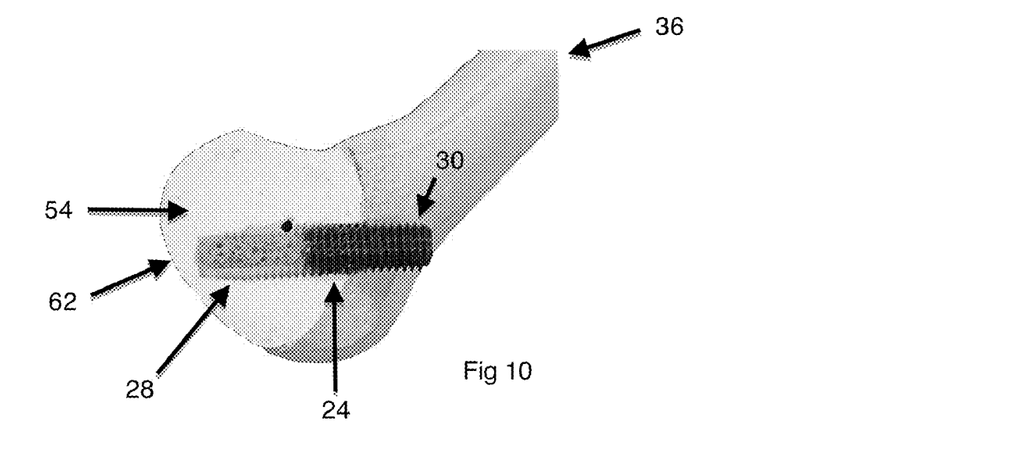
FIG. 10 shows a cross section of the femur shown in FIGS. 5-9 with the extendable component inserted through the housing, and the pressure screw beginning to engage the housing.
Figure 11:
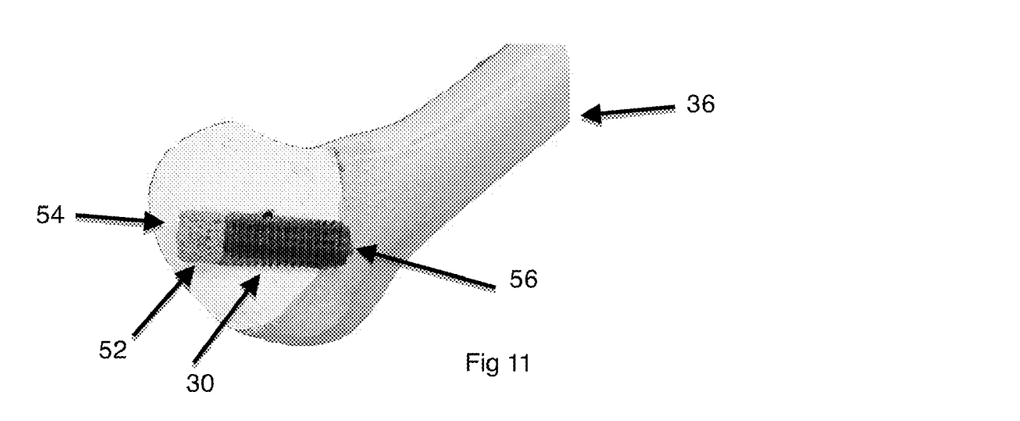
FIG. 11 shows the extendable component deformed, after it has contacted the subchondral bone at the end of the drilled hole.
Figure 12:
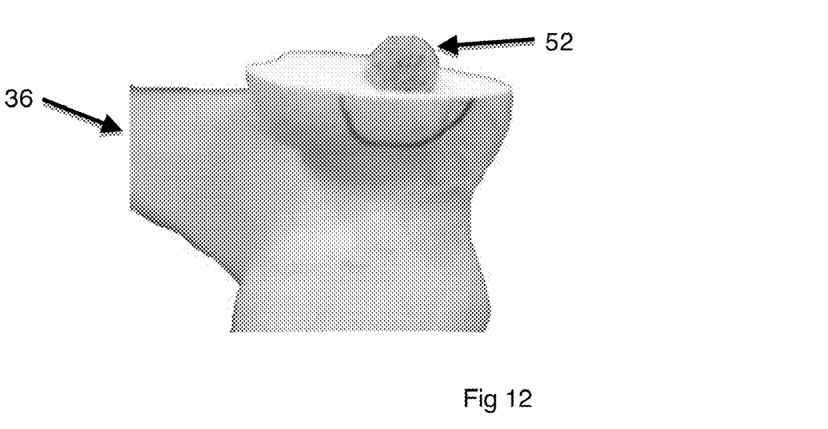
FIG. 12 shows a distal view of the deformed extendable component shown in FIG. 11.

The housing 24 is then be inserted into drilled hole 48 to a depth that provides sufficient stability and does not impinge upon other soft tissue structures in the area—see FIG. 7. The extendable component 28 can then be inserted into the housing 24, and the pressure screw 30 used to position the extendable component 24 into place—see FIGS. 8 and 9, where the pressure screw 30 is threaded into the housing 24 using a hex wrench 50. FIG. 10 shows a cross section of the femur 36, illustrating the components of the system 22—i.e., the housing 24, the extendable component 28, and the pressure screw 30—just after the pressure screw 30 has been inserted into the housing 24. After the pressure screw 30 is further threaded into the housing 24, one end 52 of the extendable component 24 deforms between the pressure screw 30 and the subchondral bone 54 of the femur 36. Finally, periodic adjustment of the pressure screw 30 can be utilized to maintain the desired amount of force as the bone adjusts to its new shape through the process. The force is applied to the bone via the deformed end 52 of the extendable component 24—see FIG. 12. A proximal end 56 of the system 22—see FIG. 11—can be further attached to the bone for additional support through the use of plates and other load distributing methods.

As described above, a housing, such as the housing 24, can be threaded directly into a femur; alternatively other mounting techniques may be used. In particular, it may be beneficial to mount a housing such that the reaction force it produces on the femur is spread over a large enough area so as to reduce the stress on the bone at its point of attachment. For example, FIG. 7 illustrates the use of a mounting plate 58, shown in phantom. The mounting plate 58 can be attached to the housing 24 by any method effective to secure it thereto. The mounting plate has four fasteners 60 used to mount the plate 58 to the femur 36. As the pressure screw 30 applies a force to the extendable component 28, the extendable component 28 impinges on the subchondral bone 54. The subchondral bone 54 is supported by cortical bone 62, which may be very strong. This creates a reaction force in the pressure screw, and therefore, the housing 24. To inhibit bone remodeling where the housing 24 attaches to the femur 36, the plate 58 distributes the reaction force, such that the pressure on this part of the femur 36 is reduced. This helps to ensure that all subsequent bone motion and/or growth occurs in the subchondral bone 54.

Once the system 22 is implanted, the mechanical fixation and subsequent ingrowth of the cancellous bone may allow for immediate weight bearing of the joint after surgery. Cement or additional mechanical fixation may also be employed to secure the exterior of the housing 24, if necessary. Adjustment of the pressure screw 24 can be made during the time of the surgery, or can be accomplished through routine office visits to minimize patient discomfort. The extendable component 28 may extend in a linear fashion in order to maximize continued biologic bony ingrowth of the surrounding bone during adjustment activities. Additional, post surgery adjustments can be employed by making a small opening in the skin above the housing 24, adjusting the pressure screw 30, and subsequently closing the wound.

In some embodiments, an inside portion of a housing, such as the housing 24, may include a planetary or similar drive mechanism. Such a drive mechanism can be driven by a micromotor, powered by an internal battery, an external leads electrical power source, or by inductive means. Adjustment of a pressure screw or similar device would then be effected by operation of the drive mechanism. Other embodiments can include the use of an electromechanical device, such as an inductive coil that forces an internal pressure component in a downward motion. The coil can be activated by placing the patient in the presence of an external radio frequency (RF) field. Such an RF field can be generated by a small device placed over the skin area near the housing.

As described above, the system and method of the present invention contemplate the application of dynamic, as well as static, loads to effect the desired bone remodeling. One embodiment of the present invention includes an electromechanical device, such as a motor or solenoid, that can apply a cyclic load to the bone, thereby causing strain on the bone to yield rapid bone deformation in a prescribed location. In one particular application, one or more piezoelectric force actuators are implanted and selectively activated to apply force at a rate of 30 Hertz (Hz) for ten minutes. The force can be set to a desired and effective level, and may depend on the size and location of the actuators. For example, in one embodiment, a force required to impart to the bone a stress of 3.7 MPa is used. Between the application of the cyclic loads, rest periods of ten minutes are provided; the cycle then resumes. An extended rest period may be provided during the evening sleeping period. Progress of the bone remodeling is monitored via non-invasive methods, with adjustments made to specific piezoelectric elements to control the results. The activation of the piezoelectric elements continues until the bone has sufficiently remodeled. The device is left on the bone to be become reactivated as necessary in the future.

Figure 13:
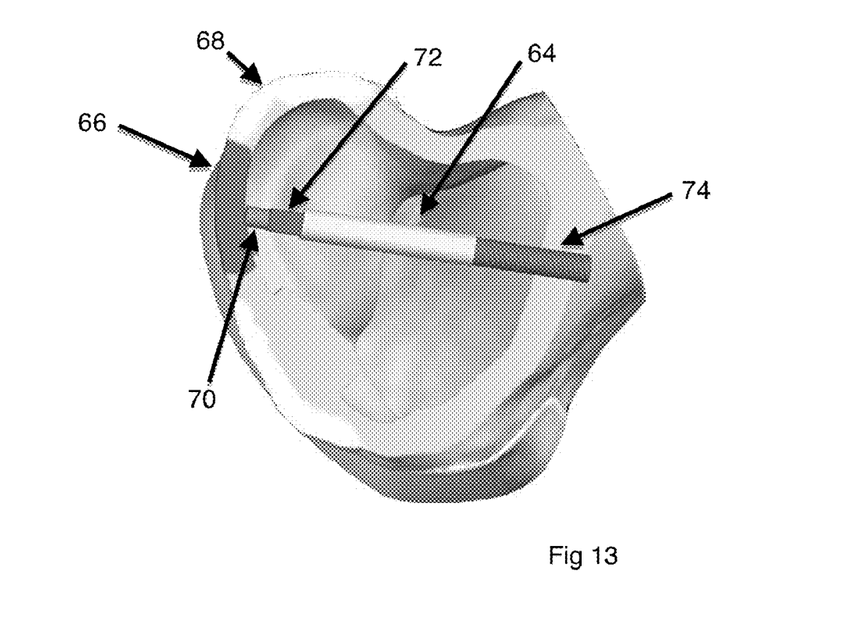
FIG. 13 shows a system in accordance with another embodiment of the present invention, the system including a linear piezoelectric actuator.

Piezoelectric actuators as described above may include, for example, linear actuators, rotary actuators, or a combination thereof. One such linear piezoelectric actuator 64 is shown in FIG. 13. As shown in FIG. 13, the actuator 64 is applying a force to the underside of an articular surface 66 of a femur 68. The actuator 64 includes an extendable component 70, which, like most typical piezoelectric devices, has a relatively small range of travel. Indeed, piezoelectric devices will often have displacements in the 100's of micrometers, which will not provide enough travel to effect desired bone growth in many patients. To overcome this limitation, the actuator 64 is provided with a secondary movement mechanism 72. The secondary mechanism 72 is configured to provide a ratcheting, positive lock that outwardly extends the extendable component 70 by some discrete amount. This allows the application of a stepwise series of 100 micrometer piezoelectric adjustments, until a total bone displacement of 1-5 mm displacement is achieved. In the embodiment shown in FIG. 13, the actuator 64 is inserted into the femur through a housing 74. The housing 74 may have internal threads to allow the actuator to be advanced in a similar fashion to the pressure screw 30 described above.

Figure 14:
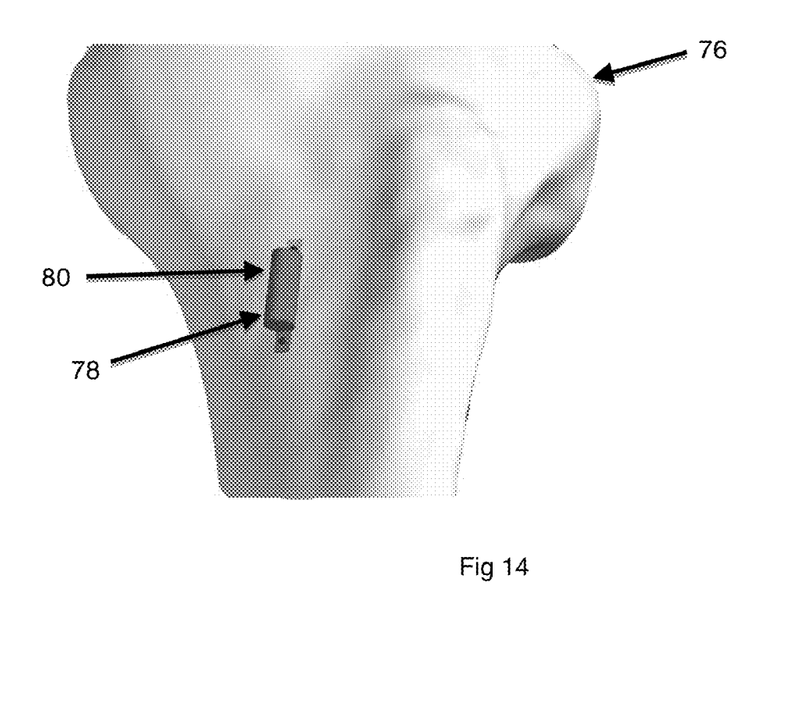
FIG. 14 shows a system in accordance with another embodiment of the present invention, the system including a linear piezoelectric actuator to increase the length of a tibia.

It is worth noting that although the systems and methods described above were used to remodel bone on the surface of an articulating joint, the invention is not so limited. Rather, the present invention has applications where shortening or lengthening of bone is desired to restore a normal joint geometry, and little or no joint surface remodeling is required. For example, a system including piezoelectric actuators can be applied to one or both sides of a joint to correct an angular displacement. For example FIG. 14 shows a tibia 76 having a system 78 in accordance with the present invention attached to it. The system 78 includes a linear actuator 80, which can be used to apply a static load, a cyclic load, or some combination thereof to the tibia 76. When a system, such as the system 78, includes two or more such actuators, one can be inserted in the cortical region and over time "grow" one side—e.g., the lateral side—and another can be inserted on the medial side to contract the bone. This effects an angular change at the joint line, and restores a more appropriate mechanical joint alignment.

Figure 15:
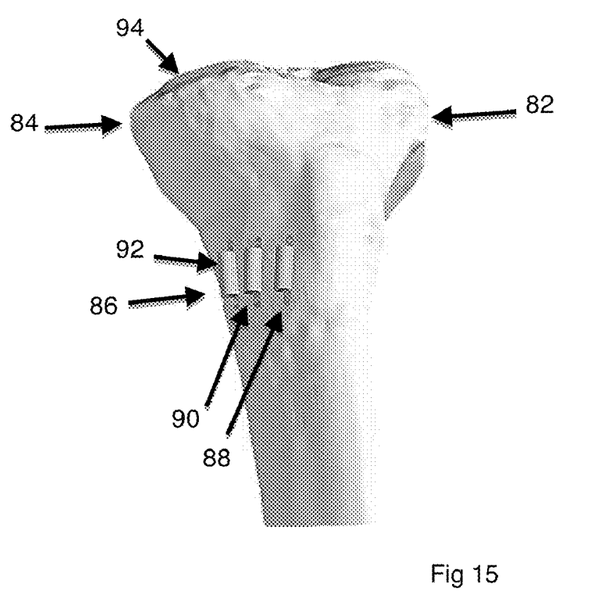
FIG. 15 shows a system in accordance with another embodiment of the present invention, the system including a plurality of linear piezoelectric actuators to increase the length of a tibia as an alternative to an osteotomy.

The present invention can also be used as an alternative to traditional procedures, such as osteotomies. For example, FIG. 15 shows a tibia 82 characterized by a loss of cartilage on its medial side 84. A system 86 of the present invention includes three piezoelectric actuators 88, 90, 92, each of which is attached to an exterior of the tibia 82 on the medial side 84. Each of the actuators 88, 90, 92 can be operated to apply an appropriate load to the tibia 82 to effect realignment of the joint space 94. Each of the actuators 88, 90, 92 can be operated with the same loading regime, or they may have individualized regimes to provide differences in the loading, and therefore the remodeling, of the tibia 82 at different locations.

Figure 16:
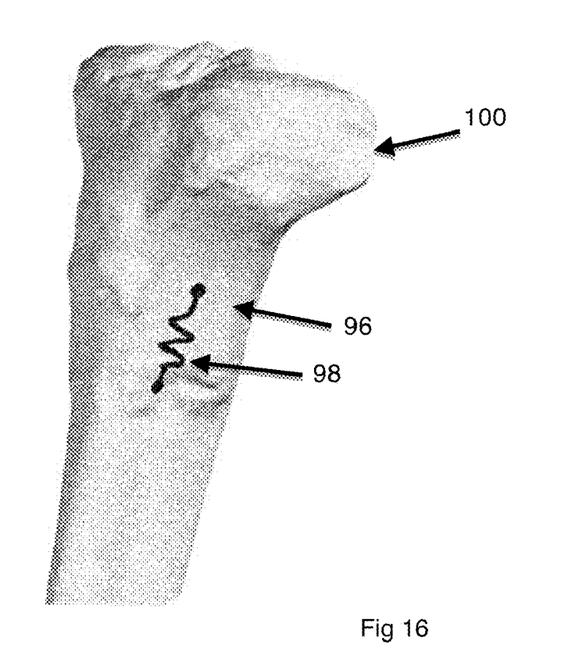
FIG. 16 shows a system in accordance with another embodiment of the present invention, the system including a shape memory alloy device configured to apply a force to a tibia when appropriate stimuli are applied.

As an alternative to, or used in conjunction with, piezoelectric actuators, other displacement mechanisms can be used in embodiments of systems and methods of the present invention. For example, a swelling memory polymer can be used to provide expansion in a predetermined direction to a predetermined volume, thereby exerting pressure against the containing tissues. Shape memory alloys, such as Nitinol (Ni-TI) can also be used. Such alloys, commonly used in bone staples, can be formed as "muscle wires" and inserted into the cortical bone, where they lengthen in response to outside stimuli. FIG. 16 shows an example of one such system 96, which includes an extendable component 98, made from Nitinol, inserted into a tibia 100. In response to an appropriate stimulus, for example an electrical current or application of heat, the extendable component 98 will provide a tensile load on the tibia 100. In other embodiments, a system, such as the system 96 may include one or more contracting elements made from a shape memory alloy. The specific requirements of configuring a shape memory alloy to expand or contract are well known to those in the art. A shape memory alloy could also be formed as a spring, and configured to lengthen (or contract) upon application of an electrical current, for example, an 80 mA current at 20C. Any of the aforementioned actuators, static or dynamic, can be combined with pulsed electromagnetic fields (PEMF) and/or Low Intensity Pulsed Ultrasound (LIPU) to further stimulate bone growth.

As an alternative to the automated loading described above, a bone remodeling system, such as the system 22—see FIG. 2—may be manually adjusted at regular intervals to provide an approximation of a slow cycle loading. To facilitate proper adjustment on any of the bone remodeling systems described herein, non-invasive monitoring may be performed on the bone itself, the actuator, or a combination of the two. For example, one or more known techniques, such as x-rays, computerized tomography (CT), magnetic resonance imaging (MRI), positron-emission tomography (PET), or other methods can be used. Moreover, biomarkers, normally found in blood serum and, or joint fluid, may be used to monitor the biologic health of the region of interest, thereby providing feedback to facilitate proper adjustments of the bone remodeling system. Adjustments can be made during routine office visits to minimize patient discomfort.

Of course, the application of one or more static loads and one or more cyclic loads are not mutually exclusive within the present invention. Rather, they may be beneficially used in concert, such the desired remodeling is achieved with a cyclic loading, and the bone density and mass are increased via static loading. Moreover, a number of parameters can be adjusted to accomplish the desired bone remodeling. For example, the location of bone growth can be controlled through appropriate placement of the force actuators, and the load itself can be controlled to achieve the desired results. The load can be controlled in terms of magnitude and the time of its application. Some examples of controllable load parameters include: whether the load cycle is constant or variable, the duration of the cyclic loading, the magnitude of the loads, the energy density, the induced strain rate, and the placement and duration of rest periods.

The present invention also includes a method wherein a bone remodeling system and method described above is used in conjunction with an articular repair technique. Embodiments of the method can include, for example, the use of a fibrous carbon fiber mat, which has typically been attached to an eburnated area of bone through an open procedure. Alternatively, a cartilage transplant procedure or even a mosaicplasty can be used. In a mosaicplasty, holes are drilled through the subchondral bone to promote bleeding and the formation of fibrocartilage in the place of native cartilage. All of these techniques can be applied utilizing an endoarticular approach of the present invention. In accordance with the invention, controlled entry into the articular joint space can be accomplished without violating the joint capsule. This provides the additional benefit of controlling the underlying support structure and shape after the surgery, and providing for an improved biologic sustenance of the patch materials.

Other embodiments may employ one or more pharmacological materials in conjunction with any of the systems described above. For example, a hormone, such as human growth factor, or drug therapy, such as Doxycylcline, may be used to enhance results. In addition, a plug from the endoarticular side of the joint surface can be inserted to support the remodeled area, and to create a revascularization of the underlying area and thus promote a re-vitalized articular region. The plug material may be seeded with undifferentiated cells that once placed in this loaded environment, respond to produce the essential biologic components of new healthy bone and articular material.

While embodiments of the invention have been illustrated and described, it is not intended that these embodiments illustrate and describe all possible forms of the invention. The words used in the specification are words of description rather than limitation, and it is understood that various changes may be made without departing from the spirit and scope of the invention.

What is claimed is:

1. A method for effecting displacement of bone for restoration of a skeletal joint using a bone restoration system, the joint including a portion of the bone having an articular surface thereon and a mating member configured to cooperate with the articular surface of the bone, the articular surface being disposed at a first position relative to the mating member, the bone restoration system including an actuator operable for cyclic, linear movement, the actuator having an extendable component and a secondary portion, the bone restoration system further including a housing configured for attachment to the bone and for securing the actuator, the method comprising:

engaging the housing in the bone at a position generally opposite an underside of the articular surface;

securing the actuator to the housing such that the extendable component is proximate the underside of the articular surface;

operating the actuator such that the extendable component applies at least one cyclic loading condition to the underside of the articular surface, thereby facilitating a structural change in the bone proximate the articular surface;

monitoring the bone for structural changes;

moving the secondary portion of the actuator relative to the housing toward the underside of the articular surface when a structural change in the bone has occurred; and removing application of the at least one cyclic loading condition when the bone has achieved a certain structural change, including a change in the position of the articular surface relative to the mating member.

2. The method of claim 1, wherein the housing includes at least one external thread for engaging the bone, and an aperture therethrough having at least one internal thread for receiving the actuator, the secondary portion of the actuator including at least one external thread for engaging the at least one internal thread in the actuator, the step of engaging the housing in the bone including creating an aperture in the bone and screwing the housing into the aperture to secure the housing to the bone with the at least one external thread on the housing, thereby making accessible an internal portion of the bone generally opposite the articular surface;

the step of securing the actuator to the housing including screwing the actuator into the aperture in the housing until the extendable component is at least within a contact distance of the underside of the articular surface; and the step of moving the secondary portion of the actuator relative to the housing toward the underside of the articular surface when a structural change in the bone has occurred includes screwing the actuator further into the housing, thereby moving the extendable component back to within a contact distance of the articular surface.

3. The method of claim 2, wherein each of the at least one cyclic loading condition is defined by at least a respective force amplitude and a respective frequency of force application.

4. A method for effecting displacement of bone for restoration of a skeletal joint, the joint including a portion of the bone having an articular surface thereon and a mating member configured to cooperate with the articular surface of the bone, the articular surface being disposed at a first position relative to the mating member, the method comprising:
creating an aperture in the bone proximate the articular surface, such that the articular surface is not penetrated;
inserting an actuator through the aperture such that an extendable component of the actuator contacts an internal portion of the bone generally opposite the articular surface;
applying at least one cyclic loading condition at a predetermined strain rate with the actuator to the internal portion of the bone through the extendable component;
monitoring the bone for structural changes;
moving a secondary portion of the actuator toward the internal portion of the bone when at least one of a structural change in the bone or physical displacement of the bone has occurred; and
removing application of the at least one cyclic loading condition when the bone has achieved a certain structural change, including a change in the position of the articular surface relative to the mating member.

5. The method of claim 4, wherein the actuator is part of a bone restoration system including a first portion having an aperture therethrough, the method further comprising:
attaching the first portion of the system to the bone such that the apertures are generally aligned;
securing the actuator to the first portion of the system to facilitate application of the at least one cyclic loading condition to the internal portion of the bone by the extendable component.

6. The method of claim 5, wherein the step of applying the at least one cyclic loading condition to the internal portion of the bone includes providing electrical power to the actuator to effect a movement thereof.

7. The method of claim 1, wherein the extendable component includes a material that is deformable when the at least one cyclic loading condition is applied to the underside of the articular surface, thereby increasing a surface area of the extendable component and distributing the stress applied to the underside of the articular surface when the at least one cyclic loading condition is applied.

8. The method of claim 1, wherein the step of moving the secondary portion of the actuator relative to the housing toward the underside of the articular surface when a structural change in the bone has occurred includes sending an electromagnetic signal to the actuator from outside the patient, thereby causing the actuator to be repositioned without an invasive procedure.

9. The method of claim 1, wherein the housing includes at least one external thread for engaging the bone, and an aperture therethrough having at least one internal thread for receiving the actuator, the actuator including at least one external thread for engaging the at least one internal thread in the housing,
the step of engaging the housing in the bone including creating an aperture in the bone and screwing the housing into the aperture to secure the housing to the bone with the at least one external thread on the housing, thereby making accessible an internal portion of the bone generally opposite the articular surface;
the step of securing the actuator to the housing including screwing the actuator into the aperture in the housing until the extendable component is at least within a contact distance of the underside of the articular surface; and
the step of moving the secondary portion of the actuator relative to the housing toward the underside of the articular surface when a structural change in the bone has occurred includes ratcheting the secondary portion outward, thereby moving the extendable component closer to the underside of the articular surface.

10. The method of claim 4, wherein the extendable component includes a material that is deformable when the at least one cyclic loading condition is applied to the internal portion of the bone, thereby increasing a surface area of the extendable component and distributing the stress applied to the internal portion of the bone when the at least one cyclic loading condition is applied.

11. The method of claim 4, wherein the step of moving the secondary portion of the actuator toward the internal portion of the bone when a structural change in the bone has occurred includes sending an electromagnetic signal to the actuator from outside the patient, thereby causing the secondary portion to be repositioned without an invasive procedure.

12. The method of claim 5, wherein the first portion includes at least one external thread for engaging the bone, the aperture in the first portion having at least one internal thread for receiving the actuator, the actuator including at least one external thread for engaging the at least one internal thread in the first portion,
the step of attaching the first portion to the bone including screwing the first portion into the aperture in the bone to secure the first portion to the bone with the at least one external thread on the first portion;
the step of securing the actuator to the first portion including screwing the actuator into the aperture in the first portion; and
the step of moving the secondary portion toward the internal portion of the bone when a structural change in the bone has occurred including ratcheting the secondary portion outward, thereby moving the extendable component closer to the internal portion of the bone.

13. The method of claim 1, wherein the step of operating the actuator such that the extendable component applies at least one cyclic loading condition to the underside of the articular surface comprises applying the load at a rate allowing the bone to remodel via a creep mechanism.

14. The method of claim 1, wherein the step of operating the actuator such that the extendable component applies at least one cyclic loading condition to the underside of the articular surface comprises applying the load at a rate above the strain response threshold.

15. The method of claim 1, wherein the at least one cyclic loading condition comprises a cyclic load applied at approximately 30 Hertz for a predetermined time, followed by a rest period and a second application of the cyclic load.

16. The method of claim 1, further comprising applying an articular repair technique to the bone.

17. The method of claim 16, wherein the articular repair technique comprises at least one of: attaching a fibrous carbon fiber mat to an eburnated area of the bone, a cartilage transplant procedure, or a mosaicplasty.

* * * * *